April 30, 1946. H. R. BOHANNON Plant Pat. 683
GERANIUM PLANT
Filed July 9, 1945
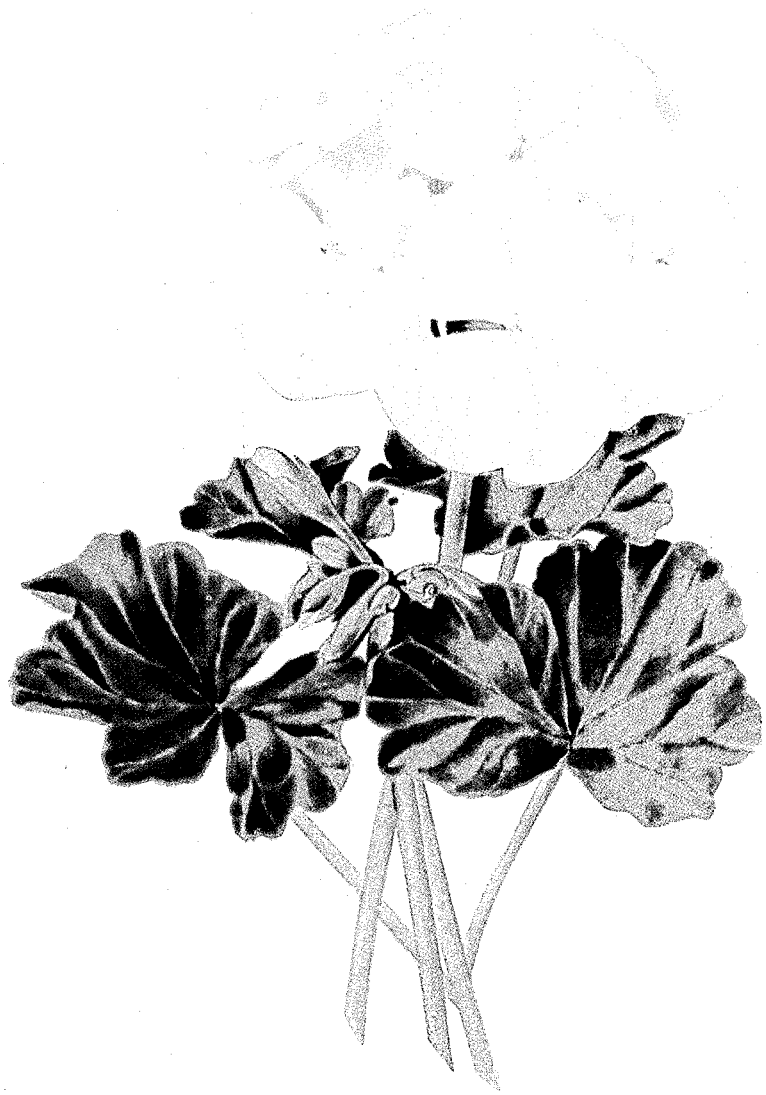
INVENTOR
Helen Roberts Bohannon
By Orville M. Kile
Plant Pat. Agt.

Patented Apr. 30, 1946

Plant Pat. 683

UNITED STATES PATENT OFFICE

683

GERANIUM PLANT

Helen Roberts Bohannon, Berkeley, Calif., assignor to Paul J. Howard Company, and Paul J. Howard's California Flowerland, Los Angeles, Calif., a corporation of California Application July 9, 1945, Serial No. 603,801

1 Claim. (Cl. 47—60)

My present invention relates to a new and improved variety of geranium plant and is the result of definite breeding efforts carried on by me to produce a variety the color of the variety Nouvelle Aurore but with a hardier constitution.

The parents of the new variety are Nouvelle Aurore and one of my unnamed seedlings. The first year's crosses resulted in a number of plants similar in color to the parent plants but of improved characteristics, including the hardier constitution sought. One of the best of these seed plants was the present variety.

My new variety differs from all varieties of geranium known to me and is the first of a new type of geranium. The plant is exceptionally free blooming, and the florets are extra large with overlapping petals and clear all-over pink. One of its most noticeable features is the globular evenness of the truss.

The illustrations show a truss of florets together with buds and leaves of my new variety in approximately their true color and also the true size in the original paintings.

Following is a description of the flower and plant of my new variety of geranium. Color plate references are to the Horticultural Colour Chart.

*The plant*

Growth: Compact and very vigorous. Attains an average height of 1 to 1½ feet in pots and 2 feet or more when grown outdoors.

Blooming habit: Continuous and exceptionally free-blooming. Plants grown in 4-inch pots produce 2 or 3 trusses at one time while full grown plants produce 40 to 50 trusses at one time.

Inflorescence: Umbel or truss.

Foliage:

*Size.*—Average to large. Leaf approximately 3 to 3½ inches in diameter.

*Color.*—Approximately Spinach Green (Ridgway's, Plate V).

*Shape.*—Disk-shaped and undulate, with deeply lobed edges.

*Texture and aspect.*—Firm; thick; upper surface smooth; lower surface moderately hairy.

Stem: Long and strong.

Petiole: Strong; slightly hairy.

Penduncle: Strong; very heavy. Color same as foliage.

*The flower*

Truss:

*Size.*—Diameter 5 to 5½ inches.

*Shape.*—Almost a perfect sphere.

*Number of florets.*—Average number of florets to a truss is 15 to 20.

*Lasting quality.*—Truss remains in bloom 10 days to 2 weeks.

Bud:

*Sepals.*—Long and pointed; about the same color as peduncle.

*Color.*—Geranium Lake (2) as bud begins to open.

*Form.*—Pointed.

Florets:

*Size.*—Averages 2½ inches in diameter.

*Petalage.*—Single row of five petals.

*Texture and aspect.*—Firm and glistening.

*Form.*—Petals are smooth edged, broad and overlapping, forming a very flat and very round floret.

*Color.*—Opening floret is approximately Begonia (619); fully opened floret is all-over Camellia Pink (622/1) from center to edge of petals with slightly darker veinings extending from center. Anthers are also slightly darker than main portion of floret. This Camellia Pink does not fade as the flower grows older.

*Lasting quality.*—Average floret lasts 2 to 3 days.

*Behavior.*—Petals drop clean, do not die on stem.

Having thus disclosed my invention, I claim:

The new and useful variety of geranium plant, substantially as shown and described, characterized particularly by its healthy growth; its continuous and exceptionally free blooming habit; its smoothly globular truss; its exceptionally large, flat florets with overlapping, even petals; and the clear all-over Camellia Pink of its florets.

HELEN ROBERTS BOHANNON.